United States Patent [19]
Gavish et al.

[11] Patent Number: 5,237,631
[45] Date of Patent: Aug. 17, 1993

[54] METHOD FOR THE MANUFACTURE OF A FLUORESCENT CHEMICAL SENSOR FOR DETERMINING THE CONCENTRATION OF GASES, VAPOURS OR DISSOLVED GASES IN A SAMPLE

[76] Inventors: Moshe Gavish; Misha Roitberg, both of P.O. Box 9263, Kiryat Bialik 27000, Israel

[21] Appl. No.: 861,130

[22] Filed: Mar. 31, 1992

[51] Int. Cl.$^5$ .............................................. G02B 6/02
[52] U.S. Cl. ..................... 385/12; 385/128; 385/141; 385/147; 422/82.08; 422/82.11
[58] Field of Search ............ 385/12, 123, 128, 141, 385/147; 422/82.05, 82.07, 82.08, 82.11

[56] References Cited

U.S. PATENT DOCUMENTS

| | | | |
|---|---|---|---|
| 4,752,115 | 6/1988 | Murray, Jr. et al. | 385/12 |
| 4,892,383 | 1/1990 | Klainer et al. | 385/12 |
| 4,925,268 | 5/1990 | Iyer et al. | 385/12 |
| 5,119,463 | 6/1992 | Vurek et al. | 385/129 |
| 5,120,510 | 6/1992 | Gourley et al. | 422/82.07 |

FOREIGN PATENT DOCUMENTS 109959 10/1983 European Pat. Off. .

*Primary Examiner*—Frank Gonzalez
*Attorney, Agent, or Firm*—Morgan & Finnegan

[57] ABSTRACT

A method for the manufacture of an improved sensor element for determining the amount of oxygen in a sample, comprises the steps of: (a) mixing a fluorescent reagent with a silicone oil which has a molecular weight of 6,700 to 80,000 and most preferably in the range of between 15,000 and 30,000; (b) heating the mixture at a temperature in the range of between 150° to 350° C. and (c) adding an optical insulating material forming an optical insulating layer onto the fluorescent reagent. Optionally, a crosslinking agent is incorporated. In order to increase the efficiency of fluorescence, an additionally layer of light scattering material is inserted between the fluorescent reagent layer and that of the insulator.

11 Claims, 1 Drawing Sheet

METHOD FOR THE MANUFACTURE OF A FLUORESCENT CHEMICAL SENSOR FOR DETERMINING THE CONCENTRATION OF GASES, VAPOURS OR DISSOLVED GASES IN A SAMPLE

The present invention relates to a method for the manufacture of a sensor for determining the oxygen content in a sample. More particularly, the invention relates to a method for the manufacture of high performance oxygen sensor having a long service time.

BACKGROUND OF THE INVENTION

The development of the optic sensors is one of the fastest growing new areas in the analytical chemistry. Most of these sensors do not involve direct analyte determination, but are measuring the optical properties of a reagent attached to the fiber distal's end. This reagent is selected to possess optical properties which are changed upon interaction with the target substrate. Fiber-optics sensors which utilize immobilized reagents have been developed based on fluorescence complexation and dynamic fluorescence quenching. Both fluorescence lifetimes and excitation/emission spectra are highly affected by immobilization method and the type of a solid support attached to the reagent. Such sensor elements, mainly for determining oxygen concentrations were developed within the last few years.

A very recent U.S. Pat. No. 4,925,268 describes a sensor suitable for monitoring the concentration of oxygen or hydrogen, using an optical fiber segment having at one end a matrix comprising an indicator molecule covalently linked to a polymer. The polymer claimed is selected from the group of acrylates and methacrylates. One of the main disadvantages of these sensors is the fact that the fluorescent reagents are characterized by strong intermolecular interactions, rendering them a very poor solubility in most of the solvents and a high tendency to aggregate and crystallize with typical columnar stacking. Moreover, the molecules of the reagent tend to migrate and aggregate within the solid polymeric matrix and thus they will lose their fluorescence property.

The effect of oxygen on fluorescent material is to reduce the intensity of the emitted radiation by providing a non radiative relaxation path for excited molecules. Generally, it is relatively quite easy to prepare a solution of one of the well known polycyclic aromatic fluorescent materials, normally used for this purpose, in a solvent such as toluene and use of this solution as an indicator. Usually this solution is encapsulated in a membrane which is permeable to a gas, so that oxygen can diffuse into the solution. It is also suggested to incorporate an indicator substance into a polymer, using the same solvent. However, after the evaporation of the solvent, the indicator generally does crystallize and thus it will loose most of its oxygen sensitivity.

In order to obviate the disadvantage of decrease in the reagent's sensitivity it was suggested in the European patent No. 109,959 to use a plasticizer as a carrier material for the indicator reagent in order to remain permanently incorporated into the polymer. In addition, it is also required a solvent for the indicator.

It is an object of the present invention to provide a method for the manufacture of a sensor for the determination of dissolved oxygen. It is another object of the present invention to provide a method for the manufacture of a sensor for determination of dissolved oxygen, said sensor possessing a very high concentration of fluorescent reagent, thus increasing the sensor's life-service use.

BRIEF DESCRIPTION OF THE INVENTION

The invention relates to a method for the manufacture of a sensor element for determining the amount of oxygen dissolved in a sample, which comprises the steps of: (a) mixing a fluorescent reagent with a silicone oil which has a molecular weight in the range of between 6700 to 80,000; (b) heating the mixture to a temperature in the range of 150° to 350° C., and (c) adding an optical insulation layer onto the fluorescent reagent. The sensor element obtained according to the present invention contains very high concentrations of the fluorescent reagent and thus it will possess high sensitivity towards oxygen. It is also characterized by its transparency to visible radiation, so that excitation and emission of light can be easily measured.

DETAILED DESCRIPTION OF THE INVENTION

Figure 1:
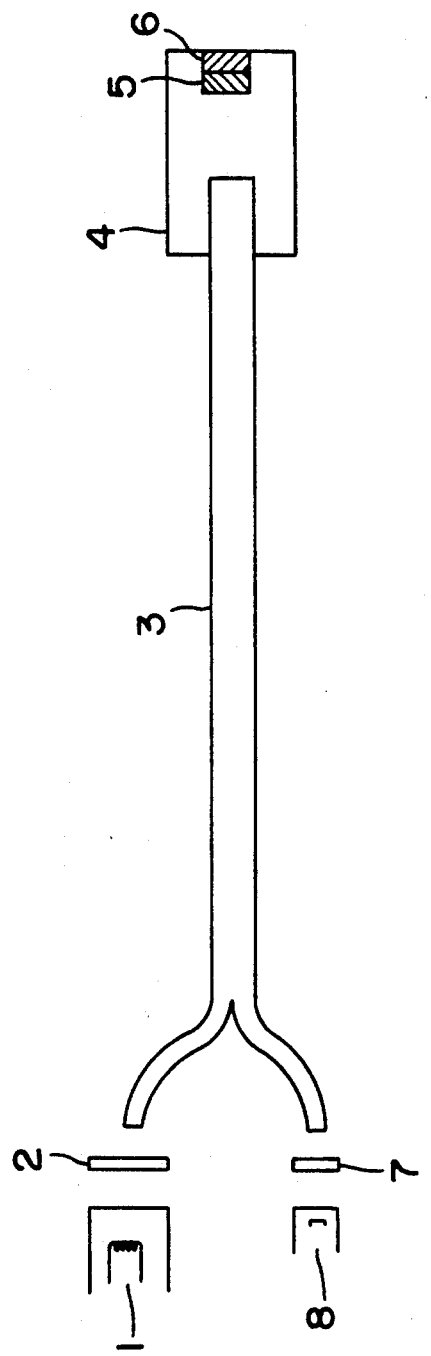
FIG. 1, is a schematic illustration of a preferred embodiment of the sensor element.

The sensor element is obtained in-situ, wherein the silicone oil having a molecular weight in the range of 6700–80,000 and preferably in the range of 15,000–30,000, serves at the same time as a solvent for the fluorescent reagent, as polymerization medium and as crosslinking agent. Silicone oils which are the main starting components for the present invention, are commercially available. They consist mainly of a mixture of dimethyl silicone, methyl-hydrogen silicone, diphenyl siloxane and methyl-diphenyl silicone. They are characterized by their excellent resistance to oxidative attack and thermal rearrangement. At a temperature of above 150° C., a gradual increase in viscosity occurs. In case of dimethyl silicone which is one of the main constituents of the silicone oil the methyl groups are oxidized to formaldehyde and then a crosslinking through the siloxane bridges takes place. Optionally an additional crosslinking agent, as usually used, such as an organic peroxide, or a diazo compound may be added.

The sensor product obtained appears as a solid possessing the mechanical properties of a highly permeable silicone rubber which entrapped a very high concentration of the fluorescent reagent. The sensor element was found to be stable at biological sterilization temperature and persists with its high permeability to oxygen.

The fluorescent reagents to be used, may be selected from various reagents known in the art for this purpose, such as polycyclic aromatic aromatic molecules, homocyclic and heterocyclic aromatic molecules. Typical examples of such compounds are: decacyclene, perylene (dibenzoanthracene), tetracene, benzanthracene, etc. A person skilled in the art will select the proper reagent according to the specific requirement for the respective use of the sensor, as well as the availability at site of the reagent.

The optical insulation layer may be selected from any known material, a preferred one being graphite powder. By incorporating this powder prior to the heating step, a black optical insulating layer is produced which protects the fluorescent reagent from the outside light, but allows oxygen diffusion to sensing the reagent.

According to another embodiment of the present invention, a pigment material is introduced into the mixture of silicone oil with the fluorescent reagent, either before or during the heating treatment. After the polymerization, the pigment will be found entrapped by the silicone polymer containing the fluorescent reagent. The pigment present in the polymer will also serve as an additional protective layer for the fluorescent reagent without decreasing its high permeability towards oxygen.

For a better understanding of the invention, a schematic illustration of a preferred embodiment of the sensor element prepared according to the present invention is presented in FIG. 1.

A light source (1) emits radiation at wavelength $\lambda_1$, filtered by an optical filter (2) and transmitted to the fluorescent reagent (5) through a bifurcated optic fiber light guide (3). The fluorescent radiation of wavelength $\lambda_2 > \lambda_1$ passes through the optic fiber (3) back to the optical filter $\lambda_2$ (7) and to the optical detector (8). An indicator holder (4) is connected to the optical fiber (3). A thin pigment layer (6) serves as light absorber to provide optical independence of the fluorescent reagent. The oxygen indicator is excited optically and emits light of different wavelengths, whose intensity or lifetime depends on the amount of oxygen present in a sample.

Among the advantages of the sensor element obtained it should be mentioned its very high sensitivity towards oxygen. Thus the relative fluorescent intensity:

$$[I(0)/I(100)-1)] \times 100$$

which is a measure of oxygen sensitivity changes by 40% by adding air to nitrogen and more than 200% by adding pure oxygen.

Although in the specification only the determination of oxygen is mentioned, one may also coneive to use the sensor element based on fluorescence quenching for the determination of pH or concentration of a gas, such as carbon dioxide, using a suitable fluorescent reagent.

According to another embodiment, an additional layer of light scattering material is inserted between the fluorescent reagent layer and insulator layer. This will be useful for increasing the efficiency of fluorescence by back scattering part of the transmitted light for the fluorescent reagent.

The invention will be hereafter illustrated by a number of Examples in order to assist a better understanding of the invention, without being limited thereto.

EXAMPLE 1

An amount of 6.3 mg of decacyclene were dissolved in a small vessel containing 1 ml of silicone oil having a molecular weight of 16,000 and viscosity of 350 cps (known under the name F-350). The mixture was heated at 300° C. for two hours, whereby the liquid became a gel and formed the transparent part of the fluorescent reagent.

The addition of fine graphite powder to the solution, carried out during the heating, formed a black optical insulator that protects the fluorescent reagent from cutside light but allows the oxygen diffusion to the sensing element.

EXAMPLE 2

An amount of 6.5 mg of decacyclene were dissolved in a small vessel containing 1 ml of silicone oil having a molecular weight of 30,000 and viscosity of 1,000 cps (known under the name F-1000). The mixture was heated at 340° C. for 90 minutes, whereby the liquid became a gel and formed the transparent part of the fluorescent material.

Test with a sensor containing this indicator, showed about 10% lower sensitivity than that obtained with the sensor as prepared in the previous Example 1, but also 10% lower time constant.

EXAMPLE 3

An amount of 6.5 mg of 9,10 diphenyl anthracene were dissolved into a vessel containing 1 ml of silicone oil having a molecular weight of 80,000 and viscosity of 12,500 cps (known under the name of F-12500). The mixture was heated at 360° C. for 2 hours, whereby the liquid became a gel and formed the transparent part of the fluorescent material.

Test with a sensor containing this indicator, showed about 20% lower sensitivity than that obtained with the sensor as prepared in Example 1, but also about 15% lower time constant.

EXAMPLE 4

An amount of 10 mg of perylene were dissolved into a vessel containing 1 ml of silicone oil as in Example 1. The mixture was heated at 260° C. for 2 hours whereby the liquid became a gel and formed the transparent part of the fluorescent material.

Test with a sensor containing this indicator showed about 50% lower sensitivity than the sensor as prepared in Example 1.

We claim:

1. A method for the manufacture of a sensor element for determining the amount of oxygen dissolved in a sample, which comprises the steps of:
   (a) mixing a fluorescent reagent with a silicone oil which has a molecular weight in the range of 6,700 to 80,000;
   (b) heating the mixture at a temperature in the range of between 150° to 350° C., and
   (c) prior to or during said heating step (b), adding an optical insulating material into the fluorescent reagent, said material forming an optical insulating layer that protects the fluorescent reagent from outside light but will allow oxygen diffusion to sensing the reagent.

2. The method for the manufacture of a sensor element according to claim 1, wherein said silicone oil has a molecular weight in the range of between 15,000 and 30,000.

3. The method according to claim 1, wherein said silicone oil comprises a mixture of dimethyl silicone, methyl hydrosilicone, diphenyl silicone and methylphenyl silicone.

4. The method according to claim 1, wherein a crosslinking agent is incorporated.

5. The method according to claim 4, wherein said crosslinking agent is selected from organic peroxides and diazo compounds.

6. The method according to claim 1, wherein the fluorescent reagents are selected from polycyclic aromatic homocyclic and heterocyclic molecules.

7. The method according to claim 6, wherein said fluorescent reagent is decacyclene.

8. The method according to claim 6, wherein said fluorescent reagent is perylene.

9. The method according to claim 1, wherein said optical insulation material is graphite powder.

10. The method according to claim 1, wherein a pigment is incorporated, being entrapped by the silicone oil.

11. The method according to claim 1, wherein an additional layer of light scattering material is inserted between the fluorescent reagent layer and the insulating layer.

* * * * *